United States Patent [19]

Amano et al.

[11] Patent Number: 5,755,229
[45] Date of Patent: May 26, 1998

[54] PULSE WAVE ANALYSIS DEVICE

[75] Inventors: Kazuhiko Amano, Suwa; Hiromitsu Ishii, Chiba; Kazuo Kodama, Yokohama, all of Japan

[73] Assignee: Seiko Epson Corporation, Tokyo, Japan

[21] Appl. No.: 774,827

[22] Filed: Dec. 27, 1996

Related U.S. Application Data

[62] Division of Ser. No. 285,378, Aug. 3, 1994, Pat. No. 5,623,933.

[30] Foreign Application Priority Data

Aug. 3, 1993 [JP] Japan .................... 5-192620
Nov. 18, 1993 [JP] Japan .................... 5-289635

[51] Int. Cl.$^6$ .................... A61B 5/024
[52] U.S. Cl. .................... 128/687
[58] Field of Search .................... 128/687

[56] References Cited

U.S. PATENT DOCUMENTS

| | | | |
|---|---|---|---|
| 4,442,845 | 4/1984 | Sigphgns | 128/687 |
| 4,771,790 | 9/1988 | Yamasawa et al. | |
| 4,836,213 | 6/1989 | Wenzel et al. | |
| 4,887,607 | 12/1989 | Beatty | |
| 4,951,679 | 8/1990 | Harada | |
| 5,103,831 | 4/1992 | Niwa | |
| 5,140,991 | 8/1992 | Niwa | 128/687 |
| 5,533,511 | 7/1995 | Kaspari et al. | 128/687 |

FOREIGN PATENT DOCUMENTS 0080778 6/1983 European Pat. Off.
3612532 10/1986 Germany.

Primary Examiner—William E. Kamm
Attorney, Agent, or Firm—Mark P. Watson

[57] ABSTRACT

A pulse wave analysis device for analyzing the condition of a human body is disclosed. A cuff band is wrapped around the tip of the second finger of a subject's hand. When the operator depresses the beginning-of-measurement key, the finger tip is pressed at various pressures by means of an air pump and a pressure sensor. Pulse wave signals at different pressure values are automatically measured by an optical fingertip plethysmogram sensor. The signals are transmitted to a CPU through a BPF, an amplifier, and an ADC. The CPU performs FFT analyses on the signals and determines to which pattern from among the patterns stored in a ROM the pattern level of the pulse wave spectrum for a given pressure value is closest, and displays the result on a display unit as a test result indicating the viscoelasticity of the subject's peripheral circulation tissue.

12 Claims, 12 Drawing Sheets a: 21-YEAR-OLD MALE   d: 34-YEAR-OLD MALE
b: 26-YEAR-OLD MALE   e: 44-YEAR-OLD MALE
c: 33-YEAR-OLD MALE   f: 58-YEAR-OLD MALE

PULSE WAVE ANALYSIS DEVICE

This is a Divisional of prior application Ser. No. 08/285,378 filed on Aug. 3, 1994 now U.S. Pat. No. 5,623,933, issued Apr. 29, 1997.

BACKGROUND OF THE INVENTION

1. Field of the Invention

The present invention generally relates to pulse wave analysis devices. More particularly, it relates to pulse wave analysis devices that analyze the condition of a living body such as a human body based on pulse waves obtained from the body.

2. Background Art

Because people today are subjected to excessive stress, concerns have arisen about sudden, stress-related death and death from fatigue. There is a pressing need for a means of analyzing such symptoms easily and accurately.

Against this background, the pulse diagnosis as practiced in non-traditional medicine, such as that exemplified by Ayurveda method in traditional Indian medicine and by the Chun, Guan, and Chi method in Chinese medicine has attracted considerable attention. According to this form of pulse diagnosis, a disease can be diagnosed accurately only when the practicing "sage" feels the patient's pulse. It would be extremely useful if the same diagnosis could be performed by a machine.

From the above standpoint there has been a need for an apparatus capable of analyzing physical symptoms by extracting the information contained in pulse waves, and the development of such an apparatus has been studied.

SUMMARY OF THE INVENTION

The inventors of the present invention have studied the relationship between pulse waves and physical health from the above standpoint with the intention of developing an apparatus capable of analyzing the state of one's health based on pulse waves. Their studies have determined that the waveform of a pulse wave changes as a function of the pressure applied at the pressure measurement site. It is well known that illness is closely related to the dynamic characteristics of a person's blood vessels. If it is possible to determine objectively the behavior of pulse waves with respect to applied pressure, the diagnosis of a patient's illness will be greatly improved both in terms of speed and objectivity. The present invention was developed against this background. Its objective is to provide a pulse wave analysis device capable of determining the behavior of pulse waves with respect to applied pressure in an objective manner.

For the implementation of the system identified above, the applicants who developed the present invention performed the following experiments in order to verify its validity:

Description of the Experiment
(1) Objects of the Experiment

Fingertip plethysmograms are blood stream pulse waves in the peripheral circulation system and can be measured non-invasively. These pulse waves are receiving increasing attention as a means of evaluating the state of peripheral circulation, the concentration of oxygen in the blood, and the extent of fatigue or stress felt by the body. In view of this fact and in order to determine non-invasively the behavior of the circulation system and the autonomous nerve system, observations were made by applying varying pressure to the peripheral tissue at the tip of a finger and by determining the resulting change in the frequency spectrum of the fingertip plethysmograms. In the peripheral circulation system the ends of the artery system, which are small arteries, divide into mesh-like capillaries which then join together to form small veins. These capillary vessels cover an extremely large total area. In parts of the body true capillary vessels can go into a collapsed state when the autonomous nervous system is excited or when the body is exposed to a low-temperature environment. This fact suggests that much information on the state of the body could be obtained from measurements of the state of these parts of the body.

(2) Experimental Method

The subject's finger was pressed against the head of an optical fingertip plethysmogram sensor in order to detect fingertip plethysmograms. The fast Fourier transform (FFT) was used to determine the spectrum for these pulse waves.

(3) Experimental Conditions

The following subjects and pulse wave measurement conditions were employed:

The first subject (subject A) was a 25-year-old male with a blood pressure of 54 mmHg over 104 mmHg. The second subject (subject B) was a 32-year-old male with a blood pressure of 58 mmHg over 96 mmHg.

Measurements were taken from each subject after the subject rested for 20 minutes, in the sitting position, after fasting. The pulse wave data were analog/digital converted every 20 milliseconds and measurements were taken for a total of 80 seconds. During the 80 second measurement time each subject was required to control his breathing at a rate of 12 inhalations per minute.

(4) Experimental Results and Discussion (4)-1 Pulse waveform relative to applied pressure FIG. 2 shows an amplified waveform of subject A's pulse wave signals at an applied pressure of 67 g/cm$^2$. The horizontal axis shows time (in seconds) and the vertical axis shows voltage (mV). This graph indicates envelope components that change relatively gradually in addition to pulse wave signals.

(4)-2 FFT analysis of pulse waveforms in FIG. 3 shows the results of FFT analysis of the pulse wave data of FIG. 2 where the horizontal axis indicates frequencies (Hz) and the vertical axis, the power (amplitudes) (mV).

In this graph the frequency component of the pulse stroke intervals (1.2 Hz) represents the fundamental wave, and its harmonic component is shown. The limit of detectability of this method is approximately 5 mV. Peak Pl that occurs at frequency 0.2 Hz in the graph appears to be a variation associated with the subject's breathing control (the 12 breathing movements per minute as noted above).

(4)-3 Relative levels of pulse wave spectra

FIG. 4 shows the relative levels of the second through eighth harmonic waves, treating the fundamental wave (1.2 Hz) as level 1, of the results of the FFT analysis of the data on subject A and of the results of the FFT analysis of similarly calculated various pressures that were applied. In this graph the horizontal axis indicates the orders of spectra and the vertical axis shows relative values.

This graph shows a variability (scattering) due to pressure differences in a range from the second to the eighth harmonic waves. This variability appears to be a characteristic of subject A.

Therefore, it appears to be possible to evaluate individual differences in peripheral circulation tissue by using the frequency components within this range of fingertip plethysmograms. If that was the case, it should be possible to achieve improvements in the S/N ratio by setting the system's low-region cut-off frequency at approximately 0.1 Hz and the high-region cut-off frequency at approximately 10 Hz.

(4)-4 Relationship between the applied pressure and the pulse wave spectra

FIG. 5 shows the amplitudes (solid line A-S1) of the fundamental wave for the pulse wave spectrum at various pressures for subject A and the amplitudes (solid line A-S2) of the second harmonic wave. The horizontal axis indicates the applied pressure (g/cm$^2$), and the vertical axis shows amplitudes (mV). Line L indicates the 5 mV amplitude level.

Similarly, FIG. 6 shows the amplitudes (broken line B-Si) of the fundamental wave for the pulse wave spectrum at various pressures for subject B and the amplitudes (broken line B-S2) of the second harmonic wave.

The graph in FIG. 7 combines the graphs of FIGS. 5 and 6 plotted together.

These graphs indicate that, in either subject A or B, both the fundamental wave and the second harmonic wave produce an approximately identical amplitude at applied pressures ranging from 17 g/cm$^2$ to 67 g/cm$^2$ with little difference between the two waves. If the pressure at which the amplitude of a spectrum falls below a specified value, i.e., 5 mV (line L), is assumed to be the pressure at which the spectrum disappears, the required pressure for the fundamental wave is 133 g/cm$^2$ for subject A and 167 g/cm$^2$ for subject B. Similarly, in the case of the second harmonic wave the amplitude is less than 5 mV for a required pressure of 100 g/cm$^2$ for subject A and 167 g/cm$^2$ for subject B. Thus, it appears that there are individual differences in the pressure at which the spectrum disappears.

Compared with subject A, subject B produces larger signals at a higher pressure range of 67 g/cm$^2$ to 133 g/cm$^2$. It is, therefore, inferred that subject B has a higher viscoelasticity in his peripheral circulation tissue than subject A does. These results suggest that conditions such as the viscosity resistance and the viscoelasticity of the peripheral circulation system can be determined from the relationship between the amount of pressure applied to the peripheral tissue at the tip of a finger and the resulting frequency spectrum of the fingertip plethysmogram.

This present invention was developed based on the information obtained as described above.

The present invention provides a pulse wave analysis device which provides information indicating the status of a living body. In order to obtain such information, the pulse wave analysis device detects pulse waves from the living body and the pressure applied at the site on a body surface of the body at which pulse waves are detected. The pulse wave analysis device identifies a pulse wave variation pattern of the pulse waves thus detected corresponding to a change in the pressure that is applied at the detection site.

The variation pattern thus identified provides useful information with respect to the illness or symptoms of the living body.

In order to detect the pulse waves at a desired condition, a pressurization means may be employed in the pulse wave analysis device to apply the desired pressures at the pulse wave detection site on the body surface of the body.

Furthermore, a pressure control means may be preferably employed in the pulse wave analysis device for stepwise varying the pressure applied by the pressurization means at the detection site.

In this device, the pulse waves corresponding to the pressures applied at the detection site are detected and the above-described variation pattern is determined based on the pulse waveforms thus detected and the pressures thus applied.

A cuff band for wrapping around a part of the body and an air pump that supplies air to the cuff band are employed as the pressurization means. In this device, the pressure control means regulates the amount of air supplied from the air pump to the cuff band so that the pressure applied at the detection site equals a target value.

A target establishing means may preferably be used in the device for establishing target pressure value to be applied at the detection site.

A display means may preferably be employed in the device for displaying a graph of the target pressure value established by the target establishing means and the detected pressure. The device enables the pulse wave detection to detect pulse waves when the pressure detected by the pressure detection means is within the predetermined range corresponding to a target pressure value.

The target pressure value may be sequentially and stepwise varied and the pulse wave variation patterns are identified based on the detected pulse wave at the various pressure values.

The frequency analysis may be performed in order to determine the variation pattern. In this case, the variation pattern of the pulse waveforms is obtained by determining the spectral change patterns that correspond to a change in pressure as obtained by the frequency analysis.

In the above case, a pattern memory may preferably be employed in the pulse wave analysis device for storing the pulse wave spectra, corresponding to the pressures applied at the detection site, as patterns for each predetermined body condition. The pulse wave analysis device uses the pattern that is closest, among the patterns stored in the pattern memory, to the pulse wave spectrum corresponding to the pressures determined by the frequency analysis to identify the pulse wave variation patterns.

The pulse wave analysis device may be designed so as to determine pressure values at which the amplitudes of the pulse wave spectra corresponding to the various pressures are less than a specified value.

In the pulse wave analysis device, waveform shape analysis may be preferably performed to detect the level ratios of the peaks that appear in the detected pulse waves, and the rise time of the pulse waves. In this case, the pattern is determined as a pattern of change in level ratios and rise times corresponding to pressure changes.

In the above case, the pattern memory stores as patterns, both the level ratios corresponding to pressure changes and changes in rise time, for each predetermined body condition. Thus, the pulse wave analysis device can output the pattern that is closest, among the patterns stored in the pattern memory means, to the pattern of change in level ratio and rise time as detected by the waveform shape analysis.

The waveform shape analysis may be performed to detect the level ratios of the peaks that appear in detected pulse waves and the rise time of the pulse waves. The device may determine the level ratios corresponding to pressure changes and a pattern of change in rise time.

The pattern memory may be employed to store as patterns, both the level ratios corresponding to pressure changes and changes in rise time, for each predetermined body condition. This device can select and output the pattern that is closest, among the patterns stored in the pattern memory means, to the pattern of change in level ratio and rise time as detected by the waveform shape analysis.

The waveform shape analysis may be performed to detect both the time ratio of the pulse wave stroke period as detected, to the length of time in which the waveform value of the pulse waves becomes greater than a specified value, and the rise time of the pulse waves. This device can determine the time ratio corresponding to a pressure change and the pattern of change in rise time.

The pattern memory may store, as patterns, both the time ratios corresponding to pressure changes and changes in rise time, for each predetermined body condition. This device can select and output the pattern that is closest, among the patterns stored in the pattern memory, to the pattern of change in time ratio and rise time as detected by the waveform shape analysis.

In an embodiment of the present invention, the magnitude of the pressure applied to the body is varied stepwise, and the magnitude of the pressure is detected. The pulse waves corresponding to the various pressures are detected from the body. The pulse wave analysis device determines the pressure at which pulse waves satisfy specified conditions. More specifically, the pulse wave analysis device determines the pressure that maximized the ratio of the size of the peak of the overlapping waves to the size of the drive waves and performs a diagnosis based on the rise time of the pulse waves at that pressure.

The device may determine the pressure that maximizes the ratio of the stroke period of the detected pulse wave to the time when the waveform value of that pulse wave becomes greater than or equal to a specified value, and may perform a diagnosis based on the rise time of the pulse waves at that pressure.

Power may be supplied through the use of the switching means only, from the time the beginning of an analysis is indicated by the user to the time the end of the analysis is indicated. Also, power may be supplied for a specified period of time through the use of the switching means, and the power supply operation is repeated at specified time intervals. Power may be supplied for a specified period of time through the use of the switching means from the time the beginning of an analysis is indicated by the user to the time the end of the analysis is indicated. Power supply operation is repeated at specified time intervals. Thus, the switching means can reduce power consumption by portable equipment.

Other objects and attainments together with a fuller understanding of the invention will become apparent and appreciated by referring to the following description and claims taken in conjunction with the accompanying drawings.

DESCRIPTION OF THE PREFERRED EMBODIMENTS

The following is an explanation of the embodiments of the present invention with reference to drawings.

Pulse waves are information that can be measured, either invasively or noninvasively, on a human body. Non-invasive methods for the determination of pulse waves include the determination of change in the lateral pressure in the blood vessel as a function of the output of blood from the heart and the determination of change in blood volume in a blood vessel. Specific means of detection that are employed include light (visible and near-infrared), sound (audible and ultrasonic), and electromagnetic waves.

The embodiments described below are based on the above research results conducted by the inventors. Specifically, they are designed to exploit the following:

When fingertip plethysmograms are measured by applying pressure at a subject's finger tip, individual differences can be detected in the relationship between the magnitude of the pressure thus applied and the frequency spectra of the fingertip plethysmograms. These differences originate from the particular condition of the subject's circulation system. The embodiments refer to a pulse wave analysis device that uses near infrared radiation as a means of detection.

First Embodiment

Figure 1:
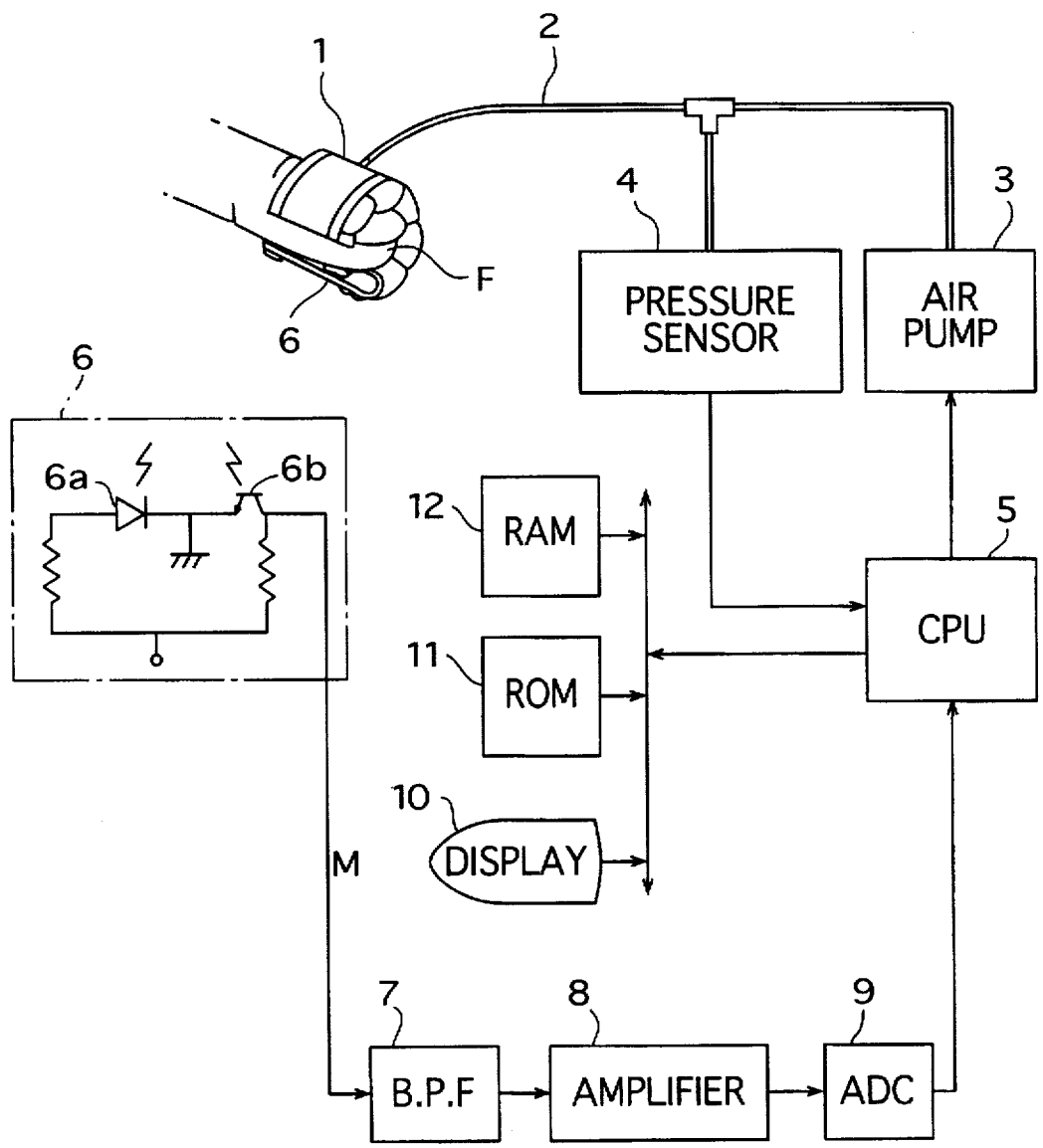
FIG. 1 shows the configuration of the pulse wave analysis device according to the first embodiment of the present invention.

FIG. 1 shows the configuration of the pulse wave analysis device according to the first embodiment of the present invention.

Configuration of the Embodiment (1) Pulse wave measurement system

In FIG. 1, a cuff band 1 is wrapped around the tip of either the right or left second finger of the subject. An air tube 2 is provided as an air conduit between the cuff band 1, the air pump 3, and the pressure sensor 4.

Under the control of CPU 5, the air pump 3 supplies the air to the cuff band 1 through the air tube 2. The air increases the thickness of the cuff band 1 and causes it to squeeze finger tip F.

The pressure sensor 4 detects the air pressure supplied to the cuff band 1 through the air tube 2 and transmits the results to CPU 5.

An optical pulse wave sensor 6 is provided inside the cuff band 1 in order to sense the fingertip plethysmograms of subjects. The optical fingertip plethysmogram sensor 6 is composed of an infrared (940 nm wavelength) light-emitting diode 6a and an optical sensor 6b.

The light emitted by the infrared light-emitting diode 6b is reflected through the blood vessels at finger tip F and is picked up by the optical sensor 6b, where it undergoes a photoelectric conversion. Pulse wave signal M at finger tip F is detected by this process.

(2) Signal processing and the control system

A band filter (hereinafter "BPF") 7 has a pass region of 0.02 Hz to 10 Hz. An amplifier 8 has a gain of 36 dB.

The analog/digital converter ADC 9 converts the pulse wave signals (analog signals) supplied through BPF 7 and amplifier 8 into 8-bit digital signals that are quantized in 256 steps.

CPU 5 uses RAM 12 as a work area and performs the following processing based on the control program and control data stored in ROM 11.

a. Pressure control processing

This process detects the pressure applied at finger tip F via the pressure sensor 4 and regulates the amount of air output by the air pump 3 so that the pressure equals a target value.

Because an analysis requires the pulse waves to be measured at various pressures that are applied, CPU 10 sequentially varies the target pressure value as follows: 17, 33, 50, 67, 83, 100, 117, 133, 150, and 167 g/cm2; and performs pressure regulation at each target value.

b. Pulse wave measurement

After the pressure is set at a target value by the pressure control processing, the pulse wave measurement processing and the frequency analysis processing described below are executed. The pulse wave measurement processing reads the fingertip plethysmogram signals detected by the optical fingertip plethysmogram sensor 6 from ADC 9.

c. Frequency analysis

The frequency analysis processing applies the FFT (fast Fourier transform) to the aforementioned fingertip plethysmogram signals in order to determine the spectrum for the pulse waves. The pressure control, pulse wave measurement, and frequency analysis processes are performed for each target pressure value.

d. Analysis

Based on the pulse wave spectra for various pressure values as determined by the frequency analysis process, the analysis processing determines a change in spectral distribution as a function of a change in pressure. Specifically, for each viscoelasticity level of the peripheral circulation tissue, patterns (as determined in the above experiment) of change in amplitude level with respect to an increase in pressure are stored in ROM 11. This analysis process determines which of these patterns is closest to the spectral distribution change as a function of change in pressure, and determines the pressure at which the spectral amplitude is less than a specified value (5 mV).

e. Output

This process directs the results of analysis to display unit 10. To facilitate analyses by physicians, this embodiment provides for the display of measured pulse waves, the results of frequency analyses, the change in pulse wave spectrum as a function of pressure, and other detailed information as well as the final analytical results. The output process displays requested information from the detailed data in response to instructions entered from the keyboard (not shown in the FIG.).

B. Operation of the embodiment

The following describes how the pulse wave analysis device operates and how to use it. In order to use this device, first the cuff band 1 is wrapped around the tip of the right or left second finger of the subject, with the finger resting on the table. The operator issues the start command to CPU 5 by pressing the start key on the keyboard, which is not shown in the FIG.

Upon receiving this command, CPU 5 regulates the amount of the air output from the air pump 3 so that the pressure reaches the first target value, 17 g/cm$^2$. As the air pressure increases, the subject's finger tip, with the cuff band 1 wrapped around it, is gradually and increasingly pressed.

While monitoring the pressure values supplied from the pressure sensor 4, the CPU 5 reads pulse wave digital signals from the ADC 9 when the applied pressure reaches the target value.

The pulse wave digital signals undergo the FFT processing in CPU 5. The calculated pulse wave spectral data are written to either RAM 12 or a storage means, such as an external storage device, which is not shown in the FIG.

Then, CPU 5 regulates the amount of the air output from the air pump 3 so that the pressure reaches the second target value, 33 g/cm$^2$. And, similarly, while monitoring the pressure values supplied from the pressure sensor 4, the CPU 5 reads pulse wave digital signals from ADC 9 when the applied pressure reaches the target value, performs a spectral analysis, and stores the results. This processing is performed on each of the target pressure values mentioned above. For every applied pressure a spectral analysis of the corresponding pulse wave signals is performed and the results are saved automatically.

CPU 5 calculates the final analytical results on a subject's circulation system as indicated below. First, the CPU compares the amplitude levels of the fundamental wave with the second harmonic wave for each applied pressure, and outputs a pattern of change in amplitude level with respect to an increase in applied pressure. Based on the experimental results as described above, patterns are divided into several groups, such as five groups A-E, according to their increase/ decrease trends. For example, the patterns showing the greatest increasing trend are placed in the first group, and the patterns showing the greatest decreasing trend are placed in the fifth group. These groups are pre-recorded in ROM 11.

When a pattern on a subject is obtained, CPU 5 determines to which of the five patterns the subject's pattern is closest, or with which of the pre-recorded patterns the subject's pattern has the highest degree of correlation. As a level indicating the the viscoelasticity of the subject's peripheral circulation tissue, CPU 5 outputs on the display unit 10 the character from among A–E that most closely matches the tested pattern.

Thus, the closer the test results to "A", the higher the viscoelasticity of the subject's peripheral circulation tissue; the closer the test results to "E", the lower the viscoelasticity. Any fundamental wave amplitude less than 5 mV is shown on the display unit 10 as a "vanishing" pressure. These test results are also stored in the above-mentioned storage means.

The peripheral circulation tissue viscoelasticity levels of subjects A and B, described above, are determined as "E" and "A", respectively, and these results are indicated on the display unit (10). These subjects vanishing pressures are displayed as 133 g/cm² and 167 g/cm², respectively. By merely viewing the test results displayed automatically after a pulse wave measurement, a person can determine his own peripheral circulation viscoelasticity level.

By operating the various function keys provided on the keyboard, the operator (or the subject) can bring up various graphs of the subject's pulse wave data on the display unit 10. These graphs enable the operator (or the subject) to learn about the subject's physical health in specific detail.

The following specific types of graphs can be produced:

(1) Pulse waveform graph for each applied pressure

Figure 2:
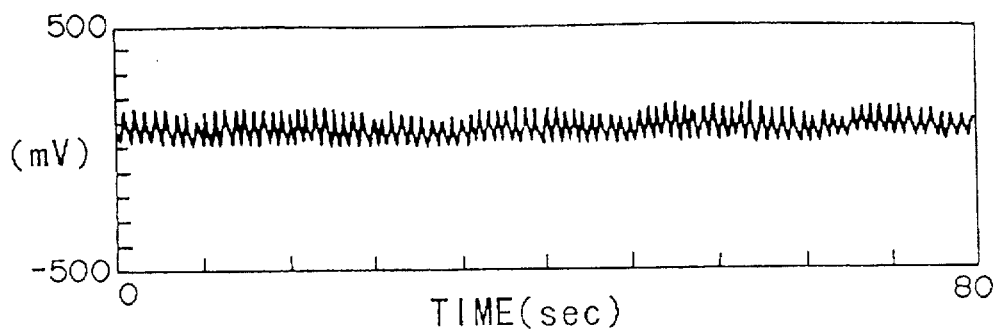
FIG. 2 is a graph of pulse waveforms at a specified pressure value for the above embodiment.

This graph corresponds to FIG. 2. This original pulse wave graph indicates whether or not there have been temporal pulse wave fluctuations as a function of applied pressure during measurement time (80 seconds).

(2) FFT analysis graph of pulse waveforms

Figure 3:
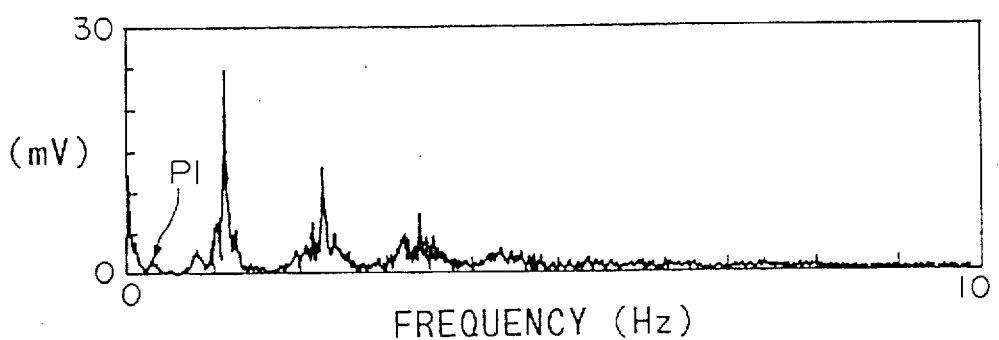
FIG. 3 is a graph of FFT analyses of the pulse waveforms for the above embodiment.

This graph corresponds to FIG. 3. This graph of amplitudes in a frequency region indicates the frequency distributions of the fundamental wave and the associated harmonic waves and the levels of these waves.

(3) Graph showing the relative levels of pulse wave spectra

Figure 4:
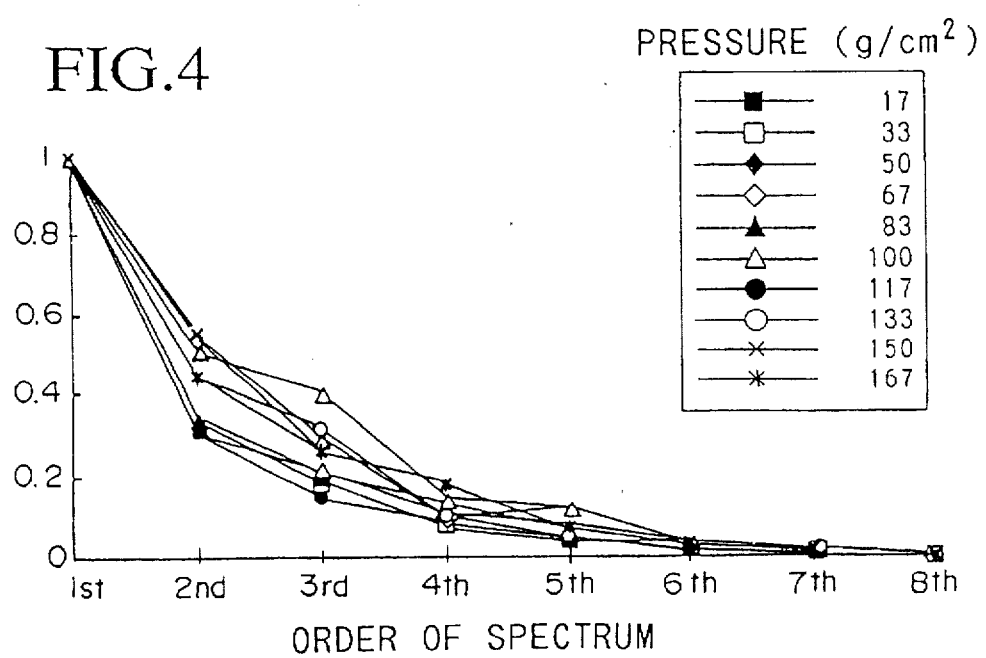
FIG. 4 is a graph of relative levels of pulse wave spectra for the above embodiment.

This graph corresponds to FIG. 4. This normalized graph can indicate whether or not there is a variation in relative level differences between harmonic waves due to differences in applied pressure.

(4) Graph of the relationship between applied pressure and the spectra

Figure 5:
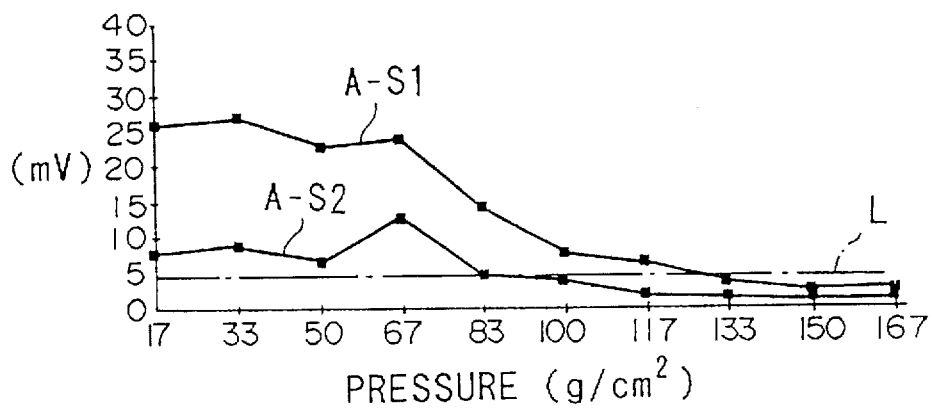
FIG. 5 is a graph which shows the relationship between applied pressure and the spectra for the above embodiment.
Figure 6:
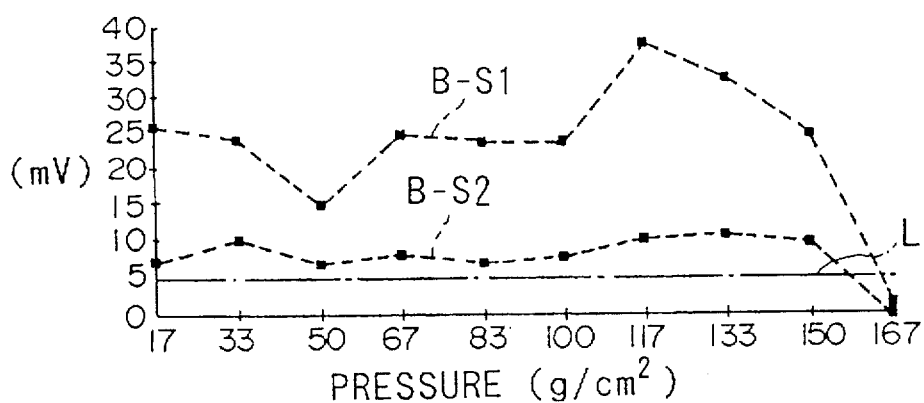
FIG. 6 is a graph which shows the relationship between applied pressure and the spectra for the above embodiment.
Figure 7:
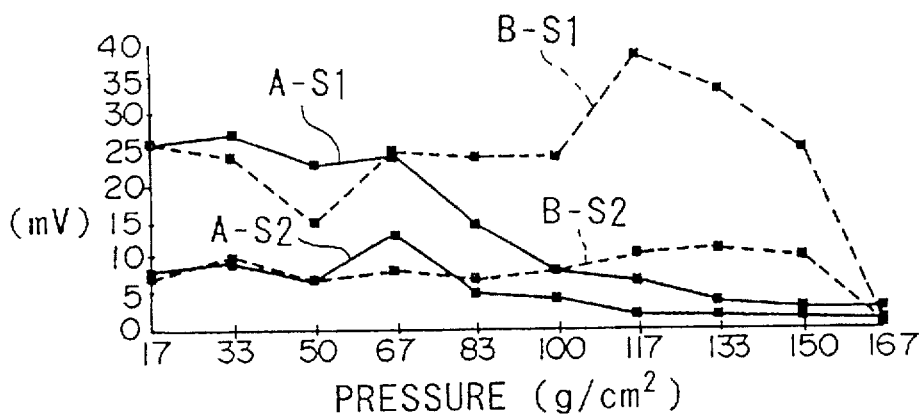
FIG. 7 is a graph which shows the relationship between applied pressure and the spectra for the above embodiment.

This graph corresponds to FIGS. 5–7. This graph indicates the type of change in amplitudes of pulse wave spectra as a function of applied pressure and the pressure level at which the pulse wave spectra vanish.

Another example of analysis

The following is an example in which the pulse wave analysis device of FIG. 1 was used to analyzed the pulse waves of other subjects under modified measurement conditions.

(1) Subjects

A total of 14 persons (10 males and 4 females) participated, ranging in age from 20 to 58.

The health status data on three representative subjects are shown below, where "Ht" indicates a blood viscosity index, "GPT" a live function index, and "TC" a lipid level value, as obtained from blood tests.

Subject C (a 33-year-old male)

Blood pressure: 110 mm Hg over 60 mm Hg

Ht: 42.4, GPT: 18, TC: 120

Subject D (a 26-year-old male)

Blood pressure: 100 mm Hg over 60 mm Hg

Ht: 43.1, GPT: 11, TC: 130

Subject E (a 34-year-old male)

Blood pressure: 144 mm Hg over 100 mm Hg

Ht: 51.9, GPT: 45, TC: 227

(2) Measurement conditions

The pass region of the BPF 7 is 0.02 Hz to 20 Hz. Amplifier 8 has a gain of 12 dB. Pressure target values are defined in 10 levels from a minimum of 20 g/cm² to a maximum of 200 g/cm², with an increment of 20 g/cm². In this experiment measurements were taken in a dark room at a room temperature of 23°±1° C., after the subject was allowed to rest for 20 minutes in the sitting position after fasting. Each subject was required to control his or her breathing at a rate of 18 breathing motions per minute for the duration of an 80-second pulse wave measurement period.

(3) Measurements and the analytical results

Figure 12:
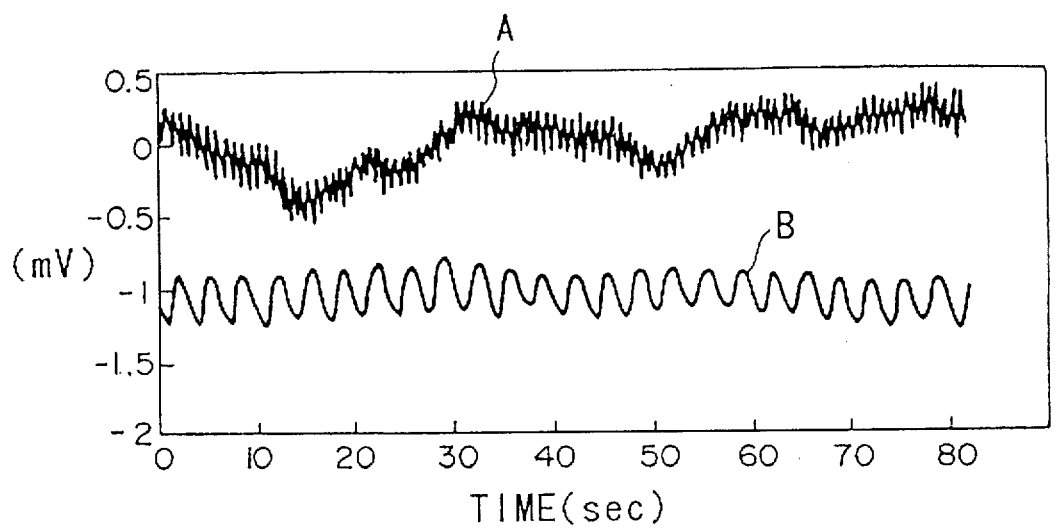
FIG. 12 is a graph which shows pulse waveforms and respiration waveforms at different pressure values for another analysis example of the first embodiment.

FIG. 12 shows the amplitude waveform (solid line A) of the pulse wave signals for subject C at an applied pressure of 40 g/cm² and the associated respiration waveform (solid line B). The horizontal axis indicates time (in seconds), and the vertical axis shows voltage (mV).

The waveform represented by solid line A indicates fluctuations that are synchronous with respiration and envelope components, originating from the autonomous nervous system function, and that change relatively slowly, as well as pulse wave signals.

Figure 13:
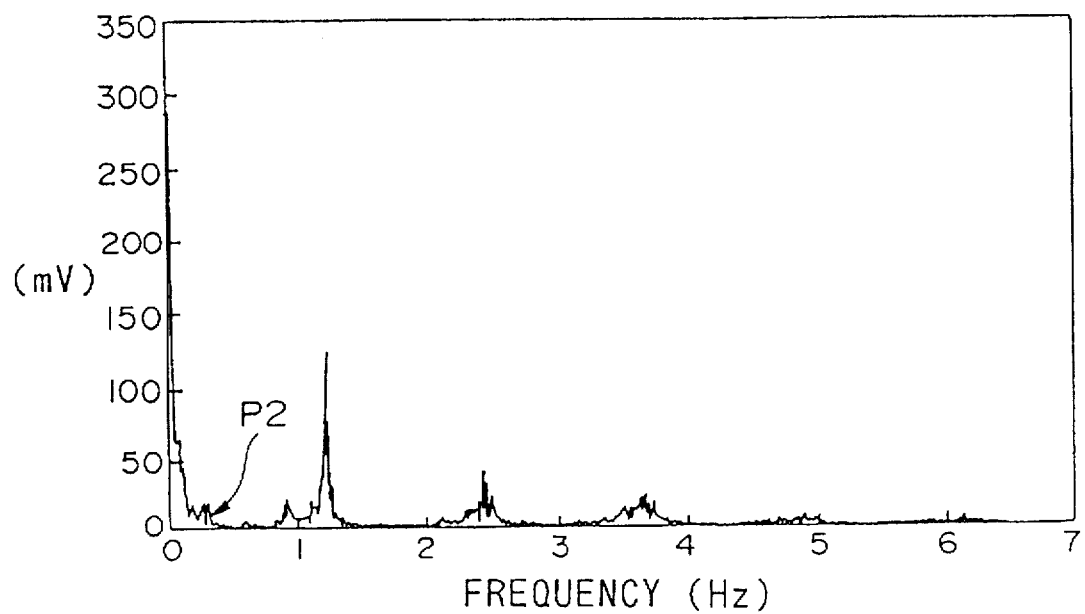
FIG. 13 is a graph which shows the FFT analysis of pulse waveforms for the same analysis example.

FIG. 13 shows the results of the FFT analysis of the pulse wave data shown in FIG. 12. FIG. 13 corresponds to FIG. 3.

In this graph peak P2, which occurs at the frequency 0.3 Hz, similar to peak P1 in FIG. 3, appears to be from fluctuations associated with the subject's breathing control (the self-regulated breathing control at a rate of 18 breathing motions per minute, as noted above).

Figure 14:
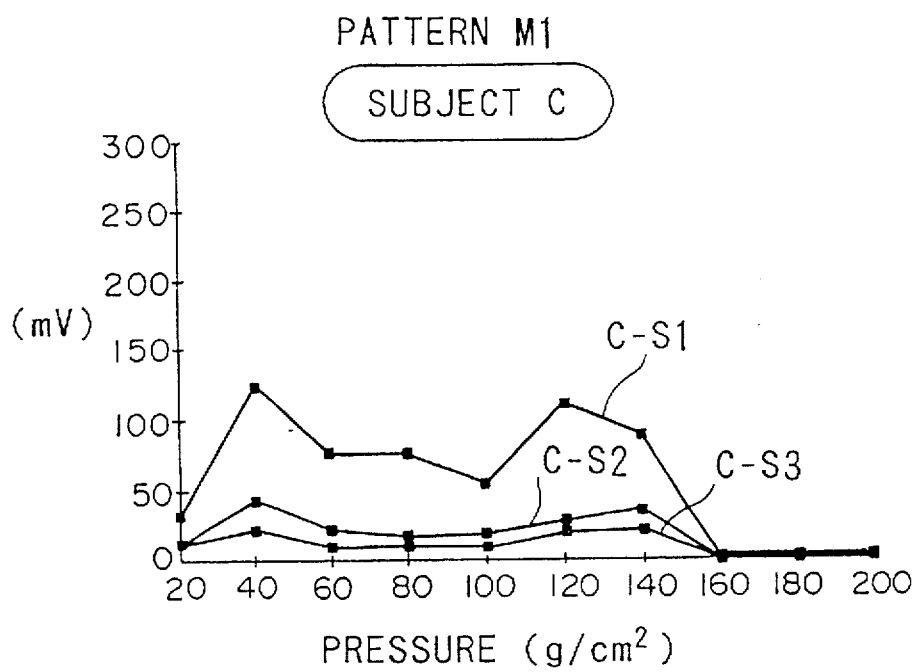
FIG. 14 is a graph which shows the relationship between applied pressure and spectra for the same analysis example.
Figure 15:
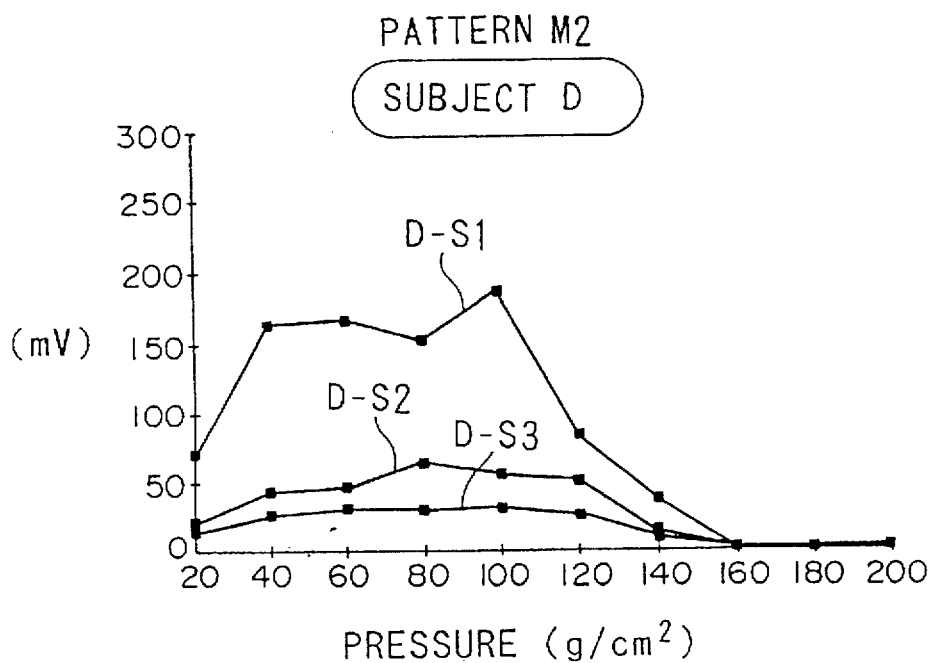
FIG. 15 is a graph which shows the relationship between applied pressure and spectra for the same analysis example.
Figure 16:
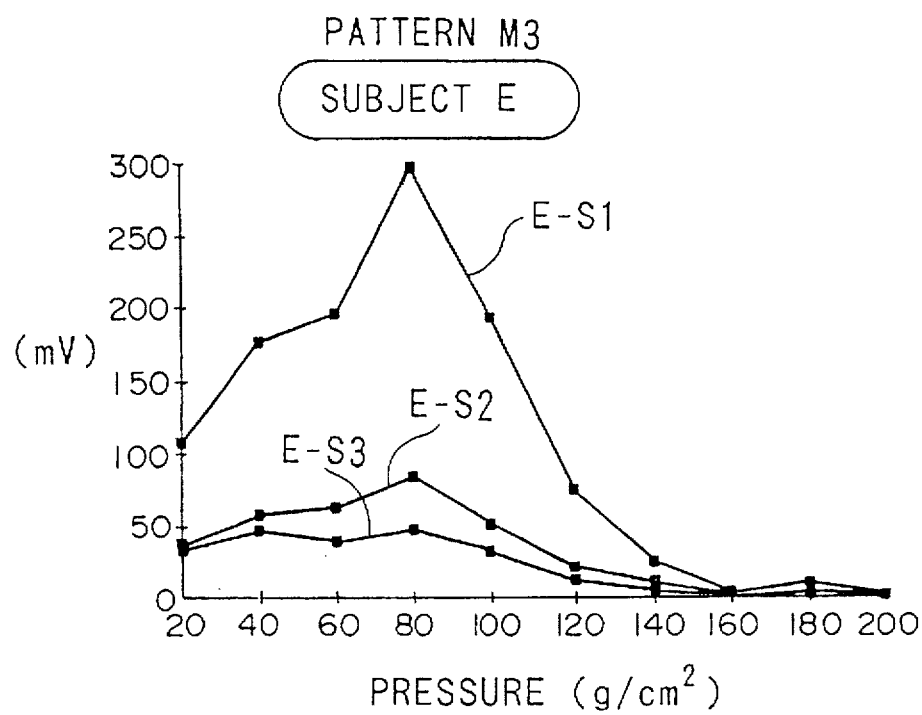
FIG. 16 is a graph which shows the relationship between applied pressure and spectra for the same analysis example.

FIGS. 14–16 show the amplitudes (solid lines C-Si, D-S1 and E-Si) of the fundamental waves, the amplitudes (solid lines C-S2, D-S2 and E-S2) of the second harmonic waves, and the amplitudes (solid lines C-S3, D-S3 and E-S3) of the third harmonic waves of the pulse wave spectra at various applied pressure values for subjects C, D, and E. The horizontal axis shows the pressure (g/cm²) and the vertical axis the amplitude (mV).

The graph in FIG. 14 shows maxima at two locations, when the applied pressure is 40 g/cm² and 120–140 g/cm², for any of the fundamental wave, second harmonic wave, or third harmonic wave amplitudes. The pattern which shows this type of change is denoted as pattern M1.

The graph in FIG. 15 shows a maximum at one location, when the applied pressure is 80–100 g/cm², for any of the fundamental wave, second harmonic wave, or third harmonic wave amplitudes. At higher pressure values the curve decreases gradually. The pattern which shows this type of change is denoted as pattern M2.

Similarly, the graph in FIG. 16 shows a maximum at one location, when the applied pressure is 80 g/cm², for any of the fundamental wave, second harmonic wave, or third harmonic wave amplitudes. Beyond this pressure value the curve decreases rapidly. The pattern which shows this type of change is denoted as pattern M3.

For the remaining 11 persons whose pulse wave spectra were measured, all spectral changes could be classified as patterns M1, M2, or M3.

The blood pressure and hematological test results of subjects C and D, whose test results match pattern M1 or M2 defined in (1) above, indicate normal values. By contrast, the blood pressure and hematological test results of subject E, whose test results match pattern M3, are higher than the normal value. Similarly, subjects who showed abnormal blood pressure and hematologocal test results as conducted by a physician produced a pulse wave spectral change pattern that matched M3.

These results suggest that the differences between these three patterns reflect differences in the viscoelasticity level of the subjects peripheral circulation tissues. Consequently, these patterns can be stored in ROM 11 for use in determining the viscoelasticity level of a subject's peripheral circulation tissue.

In these analyses, changes in pulse wave pattern in different time regions were also investigated.

Figure 17:
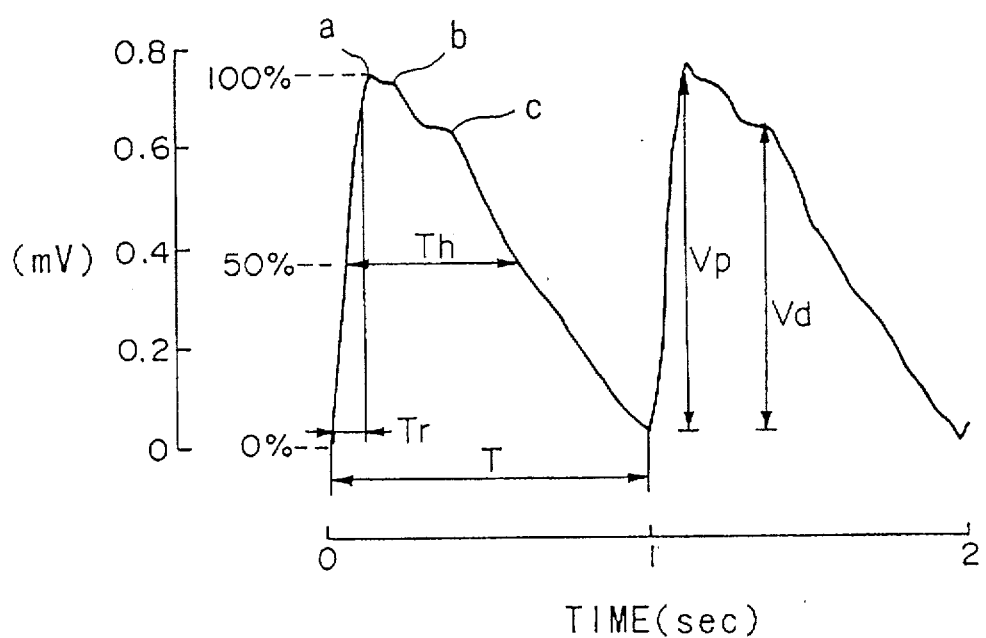
FIG. 17 is a graph of an enlargement of pulse waveforms relative to a specified pressure value for the same analysis example.

FIG. 17 is an enlargement of the amplitude waveform of subject E's pulse wave signals at the applied pressure 80 g/cm². The waveform for the output period T of pulses show waves indicated by codes a through c. Wave a is referred to as an ejection wave, b as a tidal wave, and c as a dicrotic wave. The maximum values of ejection waves and dicrotic waves are defined as peaks Vp and Vd, respectively. The time in which the first ejection wave is at a level 10% to 90% of peak Vp is defined as the rise time Tr (msec), and the time in which the level is 50% of peak Vp is defined as the half width Th (msec) of the pulse waveform.

Figure 18:
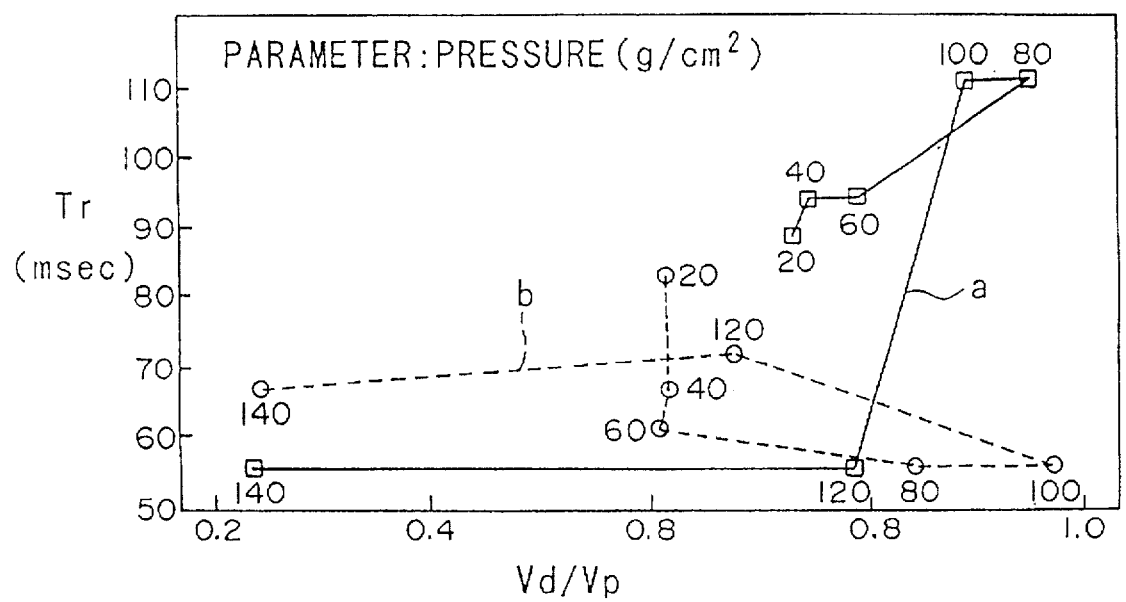
FIG. 18 shows a locus between the ratio Vd/Vp as a function of change in pressure and the rise time Tr for the same analysis example.

FIG. 18 is a graph plotting the locus between the ratios of peak values Vp to Vd (Vd/Vp) (the horizontal axis) versus rise time Tr (the vertical axis) when the applied pressure is allowed to vary from 20 g/cm² to 140 g/cm². The solid line a indicates the locus for subject C, and the broken line b indicates that for subject E.

In the case of subject C, indicated by solid line a, when the applied pressure increases over a range from 20 g/cm² to 80 g/cm², both the ratio Vd/Vp and the rise time Tr increase so that when the ratio Vd/Vp reaches a maximum, so does the rise time Tr. These two quantities decrease rapidly when the applied pressure exceeds the 100 g/cm² level.

In the case of subject E, indicated by broken line b, when the applied pressure increases over a range from 20 g/cm² to 60 g/cm², the rise time Tr diminishes while the ratio Vd/Vp remains unchanged. When the applied pressure increases over a range from 20 g/cm² to 100 g/cm², the ratio Vd/Vp increases but the rise time Tr hardly changes. Any further increase in applied pressure causes a rapid decline in the Vd/Vp ratio with little change in the rise time Tr.

The relationships between the Vd/Vp ratios and rise times Tr for the remaining 12 persons all showed loci similar to solid line a.

The pattern of change indicated by solid line a is denoted as pattern M11 and the pattern of change indicated by broken line b is denoted as pattern M12. Subject C, whose graph matches pattern M11, indicate normal blood pressure and hematological values. On the other hand, subject E, whose graph matches pattern M12, shows blood pressure and hematological test results exceeding the normal value. This subject was diagnosed by a physician as having circulation system abnormalities.

Although not shown in a figure, patterns indicated by loci between the ratio Th/T of pulse output period T to half-width period Th and the rise time Tr, when the applied pressure is allowed to vary, show similar individual differences.

From these results it appears that these pattern differences can be used to test a subject's illness. Therefore, by storing these patterns in ROM 11, it should be possible to determine a subject's physical health based on these patterns.

As described above, this embodiment permits the automatic measurement of subjects'fingertip plethysmograms relative to various applied pressure values and the objective display of the behavior of pulse waves relative to an applied pressure, based on changes in the frequency spectra of pulse waves as a function of change in applied pressure.

The illustration of the relationship between fingertip plethysmograms and applied pressure by means of various graphs enables expert analyzers to diagnose specifically the condition of a subject's circulation system by consulting the graphs.

Because these analytical results and graph data can be saved, an analysis database can be created for each subject for use in his or her health management. Further, based upon these databases, the patterns used for judging the results of analyses (patterns A through E in this embodiment) can be modified, and patterns can be subdivided into finer categories in order to construct pulse wave analysis devices that incorporate further improvements in accuracy.

Figure 19:
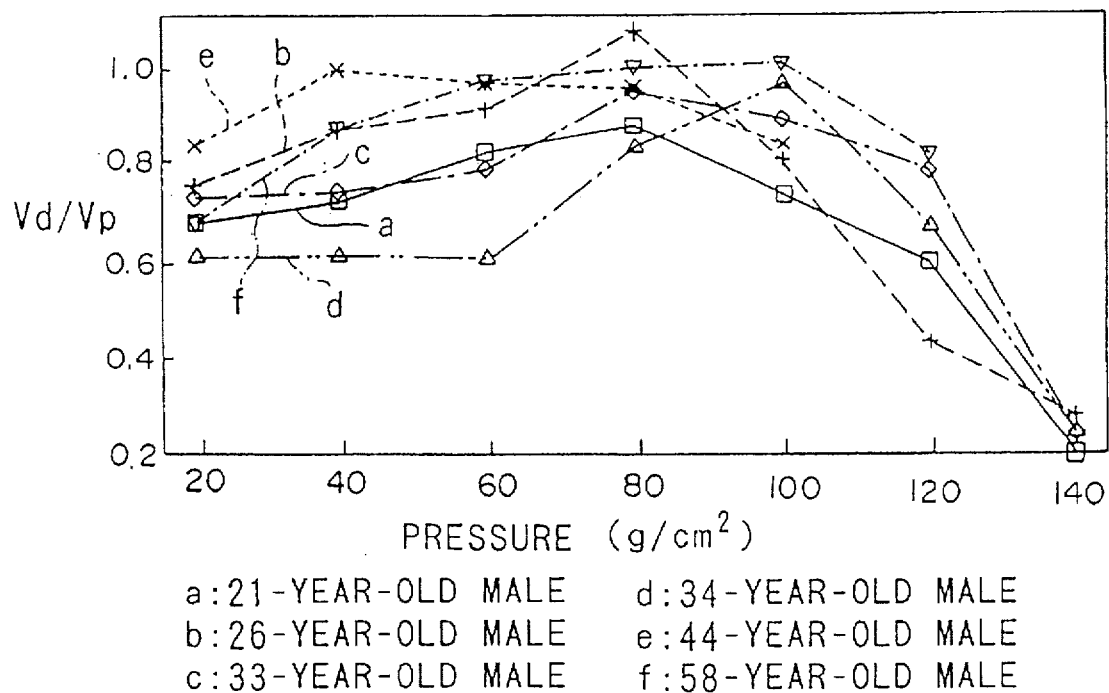
FIG. 19 shows the relationship between pressure and the ratio Vd/Vp for the same analysis example.

Further investigation by the inventors of the present invention of the data obtained as a result of these analyses produced the results shown in FIG. 19. FIG. 19 is a graph of applied pressure values (plotted on the horizontal axis) and the ratios of peak Vp of the above drive waves to peak Vd of the above superimposed waves (Vd/Vp), plotted on the vertical axis, covering six male subjects. The results indicate the occurrence of individual differences at the pressure at which the Vd/Vp ratio reached its maximum. A similar investigation of the ratio (Th/T) of pulse output period T to half-width period Th also indicates the occurrence of individual differences at the pressure at which the Th/T ratio reaches its maximum.

Figure 20:
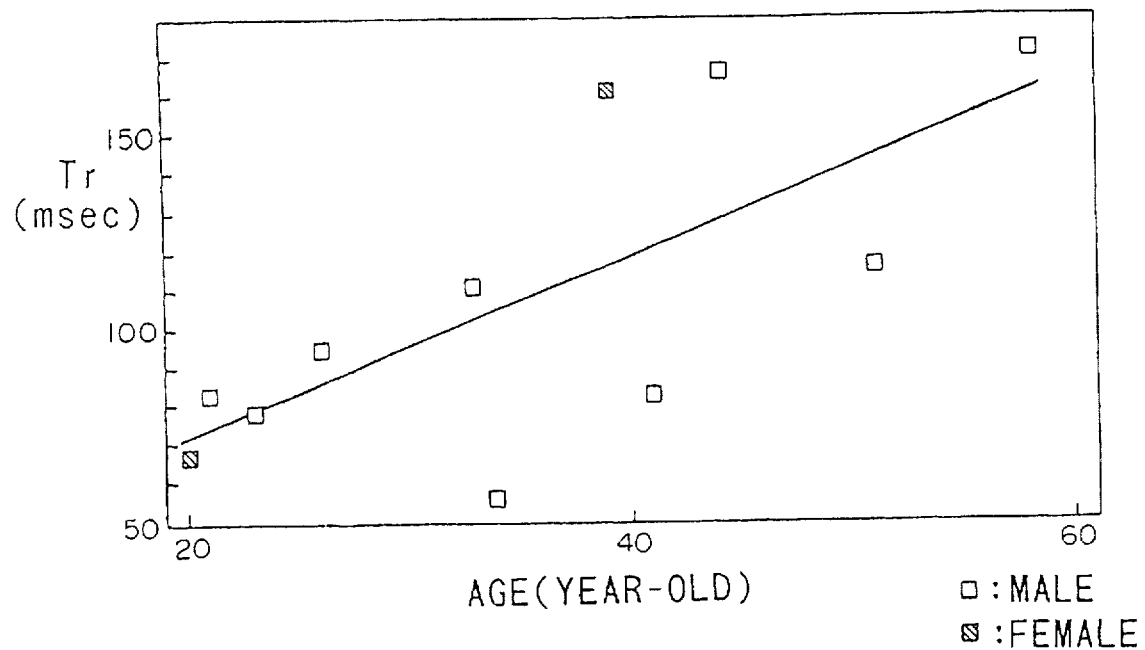
FIG. 20 shows the relationship between age and rise time Tr when pressure is applied in each subject so that the ratio Vd/Vp reaches its maximum for the same analysis example.

FIG. 20 is a graph which shows the relationship between ages (horizontal axis) and rise times Tr (vertical axis) of the subjects when pressure is applied so that in each subject the Vd/Vp ratio reaches its maximum. The results indicate a strong correlation (correlation coefficient r=0.71) between age and the rise time Tr.

Figure 21:
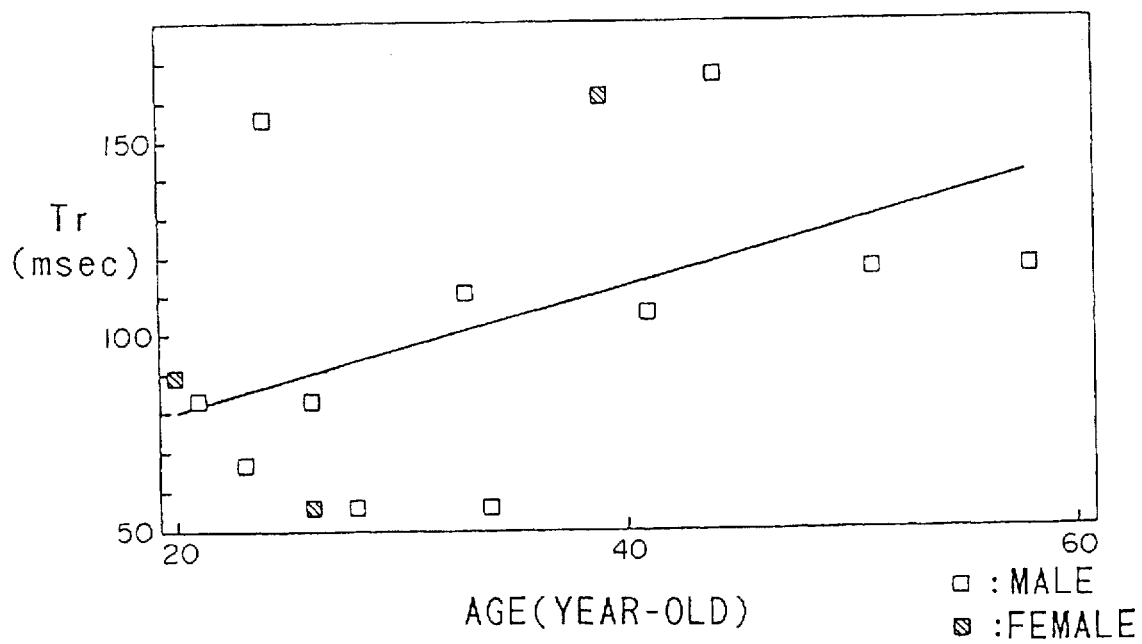
FIG. 21 shows the relationship between age and rise time Tr when pressure is applied in each subject so that the ratio TW/T reaches its maximum for the same analysis example.

Similarly, FIG. 21 is a graph which shows the relationship between ages (horizontal axis) and rise times Tr (vertical axis) of the subjects when pressure is applied so that in each subject the Th/T ratio reaches its maximum. The results indicate a considerable correlation (correlation coefficient r=0.45) between the age and the rise time Tr, although lower than the correlation that was found when, as described above, pressure was applied so that the Vd/Vp ratio reached its maximum.

Figure 22:
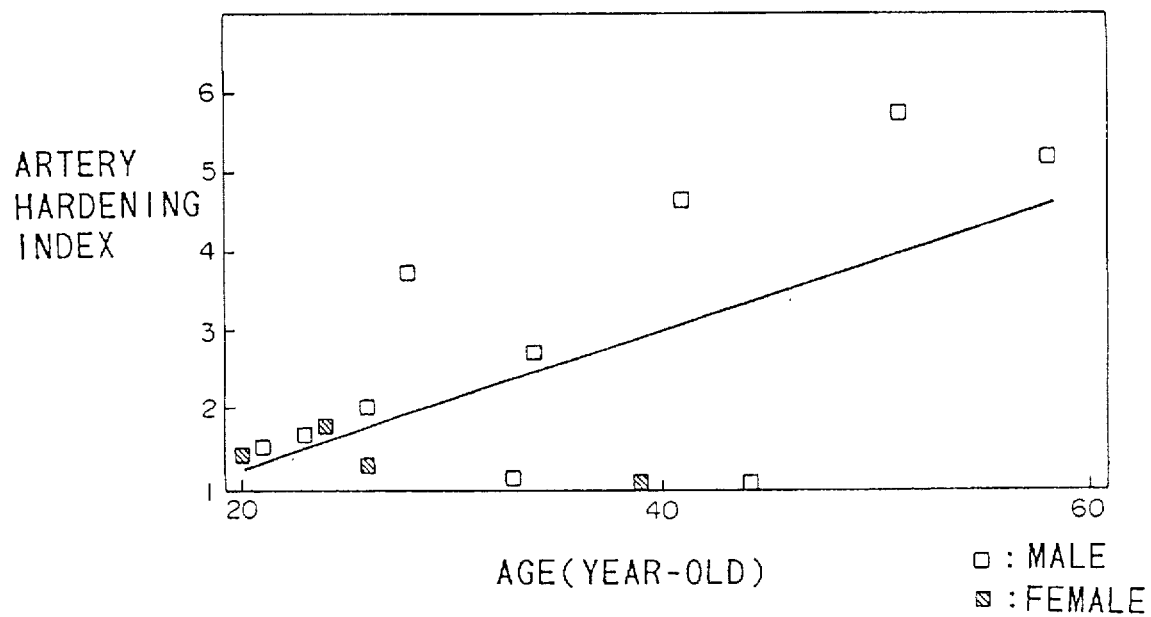
FIG. 22 shows the relationship between age and an arterial hardening index for the same analysis example.

FIG. 22 is a graph which shows the relationship between the ages (horizontal axis) of subjects and their artery hardening indices (vertical axis) as obtained from blood tests. The artery hardening index is a numerical value obtained from the total cholesterol amount (mg/dl), TCH, and the amount of high-density lipoprotein cholesterol (mg/dl), $HCL_{13}C$, according to the following formula:

$$(TCH-HCL_{13}C)/C=HCL_{13}C \tag{1}$$

Thus, the index, which is the amount of "bad" cholesterol divided by the amount of "good" cholesterol, is considered to be indicative of the extent of aging of the blood vessels. A high degree of correlation (correlation coefficient r=0.64) is also found in the relationship between age and the artery hardening index.

The results of FIGS. 20–22 suggest that it would be possible to evaluate the condition of a subject's blood vessels, i.e., the extent of their aging, by determining the rise time Tr when a pressure is applied so that either the ratio Vd/Vp or Th/T reaches its maximum in the subject. The following describes an implementation of this scheme.

The pulse wave analysis device of this embodiment has a configuration similar to that of the equipment shown in FIG. 1. This pulse wave analysis device, in its ROM (11), contains either a formula or a table indicating the correlation between rise time Tr and age, as shown by the solid lines in FIGS. 20 and 21. In this embodiment the device is operated as follows:

(1) Under the control of CPU 5, the device reads a subject's pulse waves which are determined when the pressure is allowed to vary stepwise.

(2) For each pressure value CPU 5 determines either the ratio Vd/Vp or Th/T and the rise time Tr and stores the results in RAM 5.

(3) CPU 5 selects that pressure at which either the ratio Vd/Vp or Th/T reaches its maximum and checks the corresponding rise time Tr by referencing either the above formula or the table in order to determine the extent of aging of the subject's blood vessel.

This method permits diagnoses under conditions wherein the state of a subject's blood vessels can be determined most clearly, and thus enables one to make accurate diagnoses.

Second Embodiment

This embodiment proposes a portable pulse wave analysis device that implements the pulse wave measurement function of the pulse wave analysis device described in Embodiment 1 and the function of determining the viscoelasticity of subjects'peripheral circulation tissues by means of the spectral analysis of measurement results. Specifically, this embodiment proposes a pulse analysis device that can be built into a wrist-watch.

An objective of this pulse wave analysis device is to provide a means of simple daily analyses by ordinary people for their own health management. The key considerations are ease of use and a compact design so that the pulse wave analysis device can easily fit into a wrist-watch.

A. Configuration of the embodiment

Figure 8:
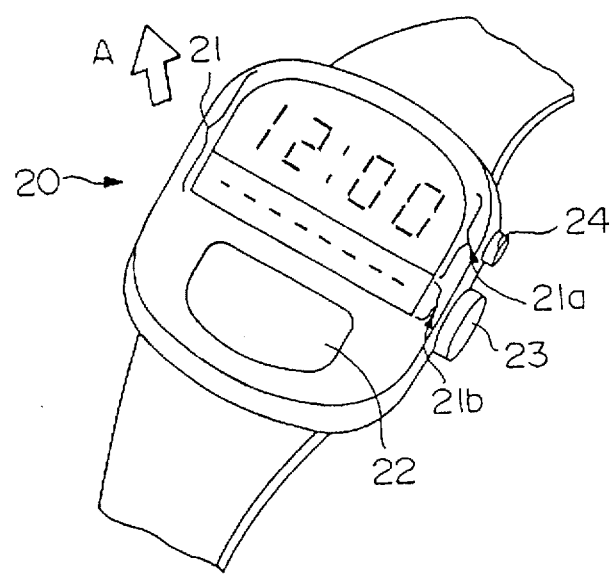
FIG. 8 shows the configuration of a pulse wave analysis device built into a wrist watch for the second embodiment of the present invention.

FIG. 8 shows the configuration of the pulse wave analysis device, built into a wrist-watch, of the second embodiment of the present invention.

In the FIG., wrist-watch 20 includes an LCD display unit 21, a finger-butt 22, a time-setting button 23, and an analysis mode button 24.

LCD display unit 21 includes a time display unit 21a and a message display unit 21b. During both normal usage and the analysis mode, the time display unit 21a indicates the current time. Because the analysis mode continues to display time, the operator, if desired, can check the current time while performing an analysis.

The message display unit 21b, during normal usage, shows the date and the day of the week. During the analysis mode it displays measurement and analysis messages and related information.

The finger-butt 22 is that part of the device against which the tip of the second finger of the hand which is not wearing the wrist-watch is pressed.

The time-setting button 23 is used to set time as in any ordinary wrist-watch. The analysis mode button 24 is used to start and stop the analysis function.

Figure 9:
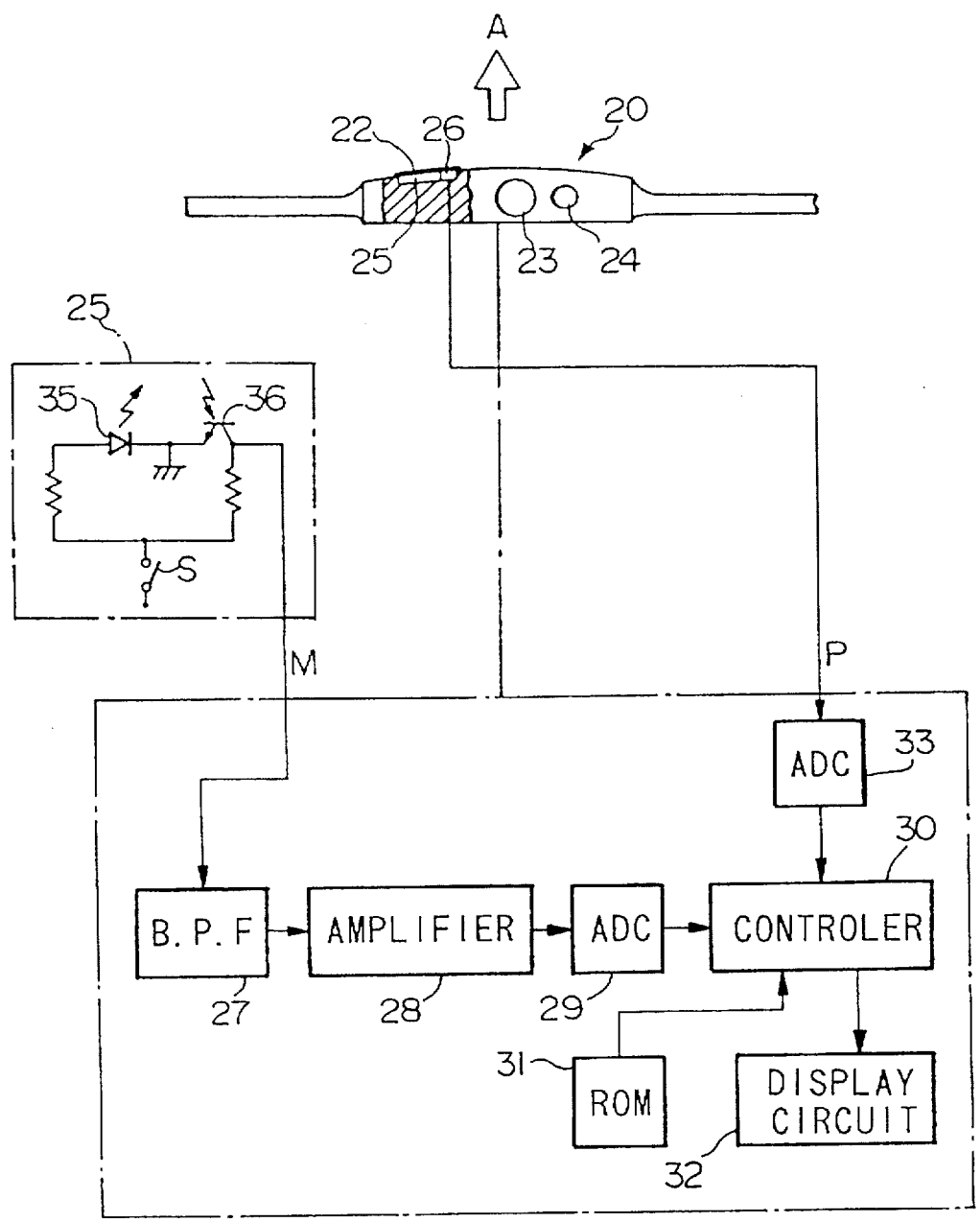
FIG. 9 shows the internal configuration of the pulse wave analysis device for the same embodiment.

FIG. 9 shows the internal configuration of the pulse wave analysis device to be built into a wrist-watch.

The underside of the finger-butt 22 is provided with an optical fingertip plethysmogram sensor 25 and a stress gauge 26.

The optical fingertip plethysmogram sensor 25 is composed of an infrared (940 nm wavelength) light-emitting diode 35 and an optical sensor (a phototransistor) 36.

The light emitted from the infrared light-emitting diode 35 is reflected through the blood vessels in the finger tip placed on the finger-butt 22, and is picked up by the optical sensor 36 where it undergoes a photoelectric conversion, thus producing pulse wave detection signal M.

Because the resistance of the stress gauge 26 varies with the amount of stress, pressure signal P that is detected is proportional to the pressure exerted by the subject's finger through the finger-butt 22.

A band filter (BPF) 27 has a pass band as in the case of Embodiment 1. An amplifier 28 which has gains that permit the type of signal processing described below. ADCs 29 and 33 are analog/digital converters (ADCs).

ADC 29 converts the pulse wave signals (analog signals) supplied through BPF 27 and amplifier 28 into 8-bit digital signals that are quantized in 256 steps. The sampling frequency f of ADC 29 is set so that it is greater than or equal to double the frequency band of the pulse wave signals.

Similarly, ADC 33 converts pressure signal P, detected by the stress gauge 26, into digital signals and outputs them.

ROM 31 stores in its memory a control program for the measurement of pulse waves, a fast Fourier transform (FFT) program that analyzes the pulse wave spectra obtained through measurement, and programs that analyze a subject's physical health based upon the results of the spectral analyses.

In this embodiment there are three patterns, A–C (rising on the right, flat, and declining on the right), that indicate the characteristics of pulse wave spectra for various pressure values. These patterns are used to analyze the condition of the subject's peripheral circulation tissue.

Controller 30 executes the programs stored in ROM 31 in order to determine the subject's pulse wave spectra at various pressure values and analyze the subject's pulse waves based on the spectra thus obtained. Specifically, the controller performs the FFT processing of the pulse wave signals output from ADC 29 and computes the level HL of their fundamental waves.

In this embodiment five gradations of applied pressure are defined: 67, 83, 100, 117, and 133 g/cm$^2$.

Unlike in the first embodiment, in this embodiment the applied pressure is not automatically controlled; rather, the amount of pressure applied depends on how firmly the subject presses his finger.

Therefore, to ensure valid measurements an appropriate, allowable range must be established for each level of applied pressure. In this embodiment an allowable range of ±2 g/cm$^2$ is defined for each of the above applied pressure values.

Controller 30 sequentially transmits to display circuit 32 message data which show the analysis procedures and graphic data which guide the user so that the subject presses on the finger-butt 22 with requisite pressure.

The display circuit 32 outputs these display data on the above message display unit 21b.

Depending on the amount of memory available in ROM 31 or the processing capacity of the controller 30, the types of analysis patterns stored in the memory for the analysis of the subject's peripheral circulation tissue viscoelasticity can be increased.

For the analysis of pulse wave spectra the levels of the second harmonic wave, as well as those of the fundamental wave, can also be computed.

To reduce the power consumption in battery-operated wrist-watches, as in the case of this embodiment, the power for the optical fingertip plethysmogram sensor 25 and for the strain gauge 26 should be turned on only when the analysis is made.

For this purpose a switch is provided on the lines that are used to supply power to the sensors. In FIG. 9, switch S is provided for the optical fingertip plethysmogram sensor 25. A similar switch is also provided for strain gauge 26. Switch drive circuits, not shown in the FIG., are provided for these switches. The circuits supply power intermittently to the various sensors by turning the switches on and off.

Figure 10A:
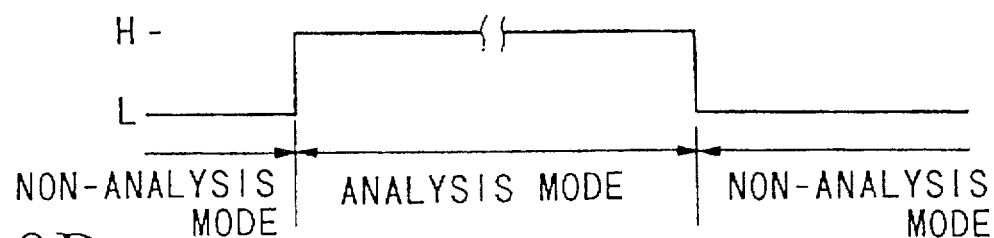
FIGS. 10A and 10B show the drive timing for the pressure detection sensor for the same embodiment.

FIG. 10A shows a timing signal that turns the switches on and off. This signal goes into the H" (high-level) state only during the analysis mode.

In FIG. 10A, during the non-analysis mode, i.e., when the wrist-watch is operating as an ordinary wrist-watch, the timing signal goes into the L" (low-level) state, during which the switches are turned off and no power is supplied to either the optical fingertip plethysmogram sensor 25 or to strain gauge 26.

When the analysis mode button 24 is pressed by the user and the analysis mode starts, the timing signal goes into the H" state which turns on the switches and supplies power to both the optical fingertip plethysmogram sensor 25 and the strain gauge 26.

When analysis mode button 24 is pressed again by the user and the analysis mode ends, the timing signal reverts to the L" state which turns off the switches and shuts off the power to the sensors.

The length of time during which the analysis mode is operative would be very small compared to the total amount of time during which the wrist-watch is worn by the user.

Therefore, the use of such a timing signal to supply power to the sensors during the analysis mode, which ensures that the current is supplied to the sensors only when the analysis mode is executed, considerably reduces overall power consumption by the wrist-watch.

Figure 10B:

As a further power-saving measure in this analysis mode, it is possible to turn the switches on and off, based on the timing action of a pulse signal (FIG. 10B) that goes into the H" state only when the pulse wave detection signal is AD-converted (analog/digital) by ADC 29, so that the output from the optical fingertip plethysmogram sensor 25 is produced only when an AD conversion is performed. A similar configuration can also be provided for the strain gauge 26.

Alternatively, regardless of whether or not the analysis mode is on, it is possible to turn the switches on and off based on the timing action of a pulse signal that goes into the H" state only when the detection signals from the sensors are AD- converted, so that the output from the sensors is produced only when an AD conversion is performed.

B. operation of the embodiment

The following is an explanation of the specific procedures for executing the analysis mode using this wrist-watch and the operation of the pulse wave analysis device. For the various execution steps the messages that appear on the message display unit 21b will also be explained in the order in which they appear.

Pressing the analysis mode button 24 enables the wrist-watch to become a pulse wave analysis device. Pressing the analysis mode button 24 for a second time returns the wrist-watch to its normal operation. Pressing the analysis mode button 24 in the midst of an analysis causes the analysis operation to be interrupted and resets the wrist-watch to its normal operation.

When the subject wearing the wrist-watch presses the analysis mode button 24, a message "PRESS UP TO 1" appears on the message display unit 21b.

Figure 11A:
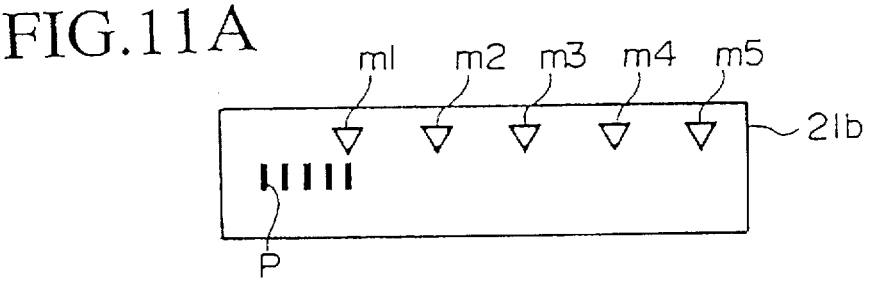
FIGS. 11A and 11B show an example of a guide message display during the operation of the pulse wave analysis device for the same embodiment.

When the subject places his finger on the finger-butt 22 and gradually presses it against the finger butt 22, the message display unit 21b changes into a graph display as shown in FIG. 11A.

In this FIG., triangle marks m1-m5 indicate the measurement points that correspond, from left to right, to the applied pressure values 67, 83, 100, 117, and 133 g/cm$^2$.

Then, bar-shaped marks, as indicated by code p, are displayed sequentially from the left. The number of displayed marks is equal to the actual amount of applied pressure as detected by the strain gauge 26. While looking at these bar-shaped marks, the subject first presses his finger against the finger-butt 22 until mark P extends to the position of mark ml which indicates the first measurement point (the condition shown in FIG. 11A).

In a condition in which mark P is displayed up to the position indicated by mark ml, the current pressure is within the allowable measurement range (±2 g/cm$^2$) for the first measurement point (67 g/cm$^2$).

If the current pressure falls outside the allowable measurement range even slightly, the P marks before and after the indicated P mark blink intermittently.

If the applied pressure falls within an allowable measurement range for a short time as described above, the graph display in the message display unit 21b terminates. When this happens, the message display unit 21b shows a "PLEASE DO NOT MOVE" message, and pulse wave signal M is detected for a specified length of time.

If the subject moves his finger during the detection period and the applied pressure detected by the strain gauge 26 deviates from the allowable measurement range, a message "REDO" appears on the message display unit 21b.

When this happens, the display on the message display unit 21b again switches to the graph display mode. At this point the subject must adjust the pressure he is applying so that mark P extends to the position of mark ml which indicates the first measurement point.

When pulse wave signal M has been detected for a specified length of time, the pulse wave data are transmitted to the controller 30 via BPF 27, amplifier 28, and ADC 29. The controller performs the FFT processing on these pulse wave data in order to calculate level EL1 of the fundamental wave.

When the measurement of the first measurement point is completed in this manner, a message "PRESS UP TO 2" appears on the message display unit 21b, and the message display unit 21b again switches to the graph display mode as described above.

Figure 11B:
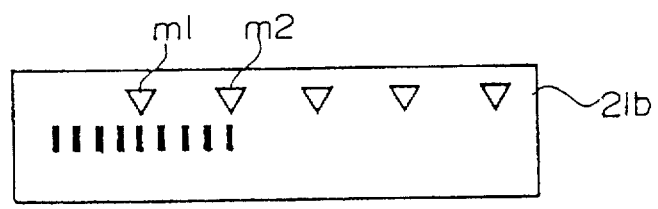

The subject then presses the finger-butt 22 somewhat more firmly so that the bar-shaped mark P extends to the position of mark ml which indicates the second measurement point (the condition shown in FIG. 11B).

The condition shown in FIG. 11B indicates that the current pressure is within the allowable measurement range (±2 g/cm$^2$) for the second measurement point (83 g/cm$^2$).

Pulse wave data are collected successively as the subject presses his finger against the finger-butt 22 successively up to the fifth measurement point according to the displayed messages. As a result, levels HL1-HL5 of the fundamental waves are calculated.

Controller 30 determines to which of the three patterns indicated above the variation characteristic of the detected levels HL1-HL5 is closest, i.e., with which pattern the variation characteristic has the highest degree of correlation.

The name of the pattern thus selected, one of the letters A through C, is displayed on the message display unit 21b.

The determination is then made as to which of the five applied pressure values causes the detection level for the fundamental wave to fall below the 5 mV level. The result of this determination is displayed in terms of a measurement point number (1-5) following the pattern name.

If none of the five applied pressure values causes the detection level for the fundamental wave to fall below the 5 mV level, the "*" symbol will be displayed in place of a measurement point number.

In the case of subject A, who was referred to in Embodiment 1, and who used the pulse wave analyses device at about the same time as the example date were collected, the test result "C5" would be displayed based upon the spectral change characteristic shown in FIG. 5.

Similarly, in the case of subject B the test result "A*" would be displayed based upon the spectral change characteristic shown in FIG. 6.

Thus, according to this embodiment the use of a pulse wave analysis device, which is built into a wrist-watch worn daily by the subject, allows him to obtain information on his peripheral circulation tissue at any time simply by pressing his finger and based upon the frequency spectrum of the pulse waves.

The effectiveness of the subject's personal health management could be enhanced, for example, if he were to perform diagnostic checks periodically and consult the physician or contact a medical care facility whenever any sudden change in analytical results occurs.

An optional memory for storing several check results can be provided so that the subject can review them periodically.

Although this embodiment uses a strain gauge as a means of detecting finger pressure as exerted by the subject, the present invention is by no means limited to this configuration. For example, the finger-butt can be a spring-based movable mechanism, wherein the level of the applied pressure is detected on the basis of the extent to which the spring stretches or contracts.

To obtain the desired pressure, in this embodiment marks m1–m5, that indicate measurement points for different pressure values, are displayed on the message display unit 21b.

On the other hand, the number of bar-shaped marks that are displayed per unit of pressure can be made inversely proportional to the target pressure value so that, whenever the target pressure changes, one mark is displayed at the same position, e.g., in the center on the message display unit 21b and also that bar-shaped marks will be displayed as successively higher values for each increase in pressure up to the indicated mark.

Also optionally indirect health tip messages 31 for different pulse wave analysis patterns can be stored in ROM so that these messages are displayed on the message display unit 21b in conjunction with the display of analytical results.

Although this embodiment uses a wrist-watch as the housing unit for a portable pulse wave analysis device, the present invention is by no means limited to this configuration. A similar pulse wave analysis device can be incorporated into any personal articles that are worn or used on a daily basis.

In the above embodiments it is also possible to test patterns of change in pulse waves, based on a variety of other characteristics, without analyzing pulse wave spectra or any of the aforementioned pulse wave characteristics (peak values Vp and Vd, and rise time Tr) that occur in the various time regions with respect to a change in the pressure applied to a given pulse wave detection site on the body.

The site for the detection of pulse waves is by no means limited to a finger tip. Toe tips or other peripheral parts of the body can also be used for the measurement of pulse waves simply by applying pressure to them.

Further, the use of the analytical device of the present invention is by no means limited to the analysis of fingertip plethysmograms as described above. The device can also be used for the analysis of radial artery pulse waves, which can be obtained by pressing the subject's wrist, as well as other types of pulse waves. Beyond the optical method used in this embodiment, acoustic, electromagnetic wave, and other means to detect pulse waves can also be employed.

While the invention has been described in conjunction with several specific embodiments, it is evident to those skilled in the art that many further alternatives, modifications and variations will be apparent in light of the foregoing description. Thus, the invention described herein is intended to embrace all such alternatives, modifications, applications and variations as may fall within the spirit and scope of the appended claims.

What is claimed is:

1. A pulse wave analysis device comprising:
    pressure detection means for detecting pressure applied at a detection site on a living body;
    pulse wave detection means for detecting pulse waves at the detection site of the body; and
    means for identifying, from among a plurality of predetermined patterns, a variation pattern of the pulse waves detected by the pulse wave detection means on the basis of changes in amplitude levels of said pulse waves corresponding to changes in the pressure applied at the detection site.

2. The pulse wave analysis device according to claim 1 further comprising pressurization means for applying pressure to the detection site on the body.

3. The pulse wave analysis device according to claim 2 further comprising pressure control means for stepwise varying the pressure applied by the pressurization means at the detection site.

4. The pulse wave analysis device according to claim 3, wherein the pressurization means comprises a cuff band for wrapping a part of the body and an air pump that supplies air to the cuff band; and
    wherein the pressure control means includes means for regulating the amount of air supplied from the air pump to the cuff band so that the pressure applied at the detection site equals a target value.

5. The pulse wave analysis device according to claim 3 wherein the identifying means comprises:
    frequency analysis means for producing pulse wave spectra of pulse waves detected by the pulse wave detection means at each applied pressure, and
    means for calculating a pulse wave spectral change pattern relative to changes in the pressure applied at the detection site based on the pulse wave spectra produced by the frequency analysis means, and
    display means for displaying a calculated change pattern.

6. The pulse wave analysis according to claim 5 further comprising
    means for measuring amplitudes of said pulse wave spectra produced by said frequency analysis means;
    means for storing a predetermined value of pulse wave spectra amplitudes;
    means for comparing said measured amplitudes to said predetermined value; and
    means for outputting pressure values at which the amplitudes of the pulse wave spectra produced by the frequency analysis means are less than said predetermined value.

7. The pulse wave analysis device according to claim 3 wherein the identifying means comprises:
    a waveform shape analysis means for detecting peaks that appear in the pulse waves detected by the pulse wave detection means and for determining levels of said detected peaks and for determining ratios of said determined peak levels and the rise time of the pulse waves at each applied pressure;
    means for calculating a pattern of changes in the level ratios and rise time relative to changes in the applied pressure.

8. The pulse wave analysis device according to claim 7 further comprising means for determining patterns of changes in level ratios and rise times relative to changes in the applied pressure and pattern memory means for storing said patterns of changes in the level ratio and rise time relative to changes in the applied pressure for each of a predetermined body condition;

wherein the identifying means further includes means for determining a pattern from among the patterns stored in the pattern memory means that is closest to the pattern of changes in level ratio and rise time relative to changes in the applied pressure calculated by the calculating means and the identifying means outputs the closest pattern as the variation pattern.

9. The pulse wave analysis device according to claim 3 wherein the identifying means comprises:

waveform shape analysis means for detecting a time of the pulse wave stroke periods and half-width periods of the pulse waves detected by the pulse wave detection means and rise time of the pulse waves at each applied pressure; and means for determining a time ratio between said pulse wave stroke periods and half-width periods; and means for calculating a pattern of changes in time ratio and in rise time relative to changes in the applied pressure.

10. The pulse wave analysis device according to claim 9 further comprising means for determining patterns of changes in the time ratio and rise time relative to changes in applied pressure and pattern memory means for storing said patterns of changes in the time ratio and rise time relative to changes in applied pressure for each of a predetermined body condition;

wherein the identifying means further includes means for determining a pattern from among the patterns stored in the pattern memory means that is closest to the pattern of changes in time ratio and rise time relative to change in the applied pressure calculated by the calculating means and the identifying means outputs the closest pattern as the variation pattern.

11. The pulse wave analysis device according to claim 1 further comprising:

means for storing a plurality of target pressure values and an allowable range for said plurality of target pressure values;

display means for displaying a graph of target pressure values to be applied at the detection site and of pressure values detected by the pressure detection means; and pulse wave detection control means for controlling the pulse wave detection means to detect pulse waves when a pressure value detected by the pressure detection means is within an allowable range of a target pressure value.

12. The pulse wave analysis device according to claim 11 further comprising means for sequentially and stepwise varying the target pressure values and issuing an instruction for pulse wave detection at each of said plurality of target pressure values to the pulse wave detection means.

* * * * *

UNITED STATES PATENT AND TRADEMARK OFFICE
CERTIFICATE OF CORRECTION

PATENT NO. : 5,755,229
DATED : May 26, 1998
INVENTOR(S) : Kazuhiko Amano, et al.

It is certified that an error appears in the above identified patent and that said Letters Patent is hereby corrected as shown below:

On the title page, item 56, References Cited, insert --Other Publications IEEE Engineering in Medicine and Biology Society, Volume 11, 9 November 1989, Seattle, Washington, US, Pages 1417-1718, Mihui Wang et al. "Non-invasive Continuous Blood Pressure Monitoring by the Unloading of Vascual Wall"--.

Signed and Sealed this

First Day of September, 1998

*Attest:*

BRUCE LEHMAN

*Attesting Officer*    *Commissioner of Patents and Trademarks*